(12) United States Patent
Schultz

(10) Patent No.: US 10,980,976 B2
(45) Date of Patent: *Apr. 20, 2021

(54) DEFLECTABLE SHEATH INTRODUCER

(71) Applicant: BIOSENSE WEBSTER, INC., Irvine, CA (US)

(72) Inventor: Jeffrey W. Schultz, Chino, CA (US)

(73) Assignee: Biosense Webster, Inc., Irvine, CA (US)

(*) Notice: Subject to any disclaimer, the term of this patent is extended or adjusted under 35 U.S.C. 154(b) by 259 days.

This patent is subject to a terminal disclaimer.

(21) Appl. No.: 16/102,008

(22) Filed: Aug. 13, 2018

(65) Prior Publication Data
US 2018/0344979 A1 Dec. 6, 2018

Related U.S. Application Data

(63) Continuation of application No. 12/346,834, filed on Dec. 30, 2008, now Pat. No. 10,046,141.

(51) Int. Cl.
*A61M 25/01* (2006.01)
*A61B 17/00* (2006.01)

(52) U.S. Cl.
CPC .... *A61M 25/0136* (2013.01); *A61M 25/0133* (2013.01); *A61B 2017/00327* (2013.01); *A61M 25/0147* (2013.01); *A61M 2025/015* (2013.01)

(58) Field of Classification Search
CPC .................. A61M 25/0136; A61M 25/0133
See application file for complete search history.

(56) References Cited

U.S. PATENT DOCUMENTS

| | | | |
|---|---|---|---|
| 4,444,195 A | 4/1984 | Gold | |
| 4,592,372 A | 6/1986 | Beranek | |
| 4,777,955 A | 10/1988 | Brayton et al. | |
| 4,930,521 A | 6/1990 | Metzger et al. | |
| 4,941,455 A | 7/1990 | Watanabe et al. | |
| 4,942,866 A | 7/1990 | Usami | |
| 4,947,827 A | 8/1990 | Opie et al. | |

(Continued)

FOREIGN PATENT DOCUMENTS

| | | |
|---|---|---|
| DE | 2752325 | 7/1978 |
| EP | 1607118 A1 | 12/2005 |

(Continued)

OTHER PUBLICATIONS

English translation of Office action dated Oct. 15, 2013, issued in JP Application No. 2009-296999, 2 pages.

(Continued)

*Primary Examiner* — Richard G Louis
(74) *Attorney, Agent, or Firm* — Lewis Roca Rothgerber Christie LLP

(57) ABSTRACT

An introducer has a shaft with a central lumen, a control handle with a deflection assembly, and a tensile member with a distal portion extending along opposing sides of within the shaft and a proximal portion extending within the control handle. The deflection assembly has a deflection arm, and a rotatable member rotationally coupled to the deflection arm, wherein the rocker member has at least one pulley engaged with the proximal tensile member portion. Rotation of the deflection arm in one direction draws the proximal tensile member portion for deflecting the shaft.

20 Claims, 15 Drawing Sheets

(56) References Cited

U.S. PATENT DOCUMENTS

| | | | |
|---|---|---|---|
| 4,996,974 | A | 3/1991 | Ciarlei |
| 5,195,968 | A | 3/1993 | Lundquist et al. |
| 5,199,950 | A | 4/1993 | Schmitt et al. |
| 5,273,535 | A | 12/1993 | Edwards et al. |
| 5,325,845 | A | 7/1994 | Adair |
| 5,328,467 | A | 7/1994 | Edwards et al. |
| 5,358,478 | A | 10/1994 | Thompson et al. |
| 5,363,861 | A | 11/1994 | Edwards et al. |
| 5,462,527 | A | 10/1995 | Stevens-Wright et al. |
| 5,545,200 | A | 8/1996 | West et al. |
| 5,626,553 | A | 5/1997 | Frassica et al. |
| 5,676,653 | A | 10/1997 | Taylor et al. |
| 5,885,288 | A | 3/1999 | Aust et al. |
| 5,891,088 | A | 4/1999 | Thompson et al. |
| 5,904,667 | A | 5/1999 | Falwell |
| 6,030,360 | A | 2/2000 | Biggs |
| 6,032,061 | A | 2/2000 | Koblish |
| 6,033,378 | A | 3/2000 | Lundquist et al. |
| 6,144,870 | A | 11/2000 | Griffin, III |
| 6,171,277 | B1 | 1/2001 | Ponzi |
| 6,198,974 | B1 | 3/2001 | Webster, Jr. |
| 6,210,407 | B1 | 4/2001 | Webster |
| 6,213,974 | B1* | 4/2001 | Smith ............... A61M 25/0136 600/139 |
| 6,224,609 | B1 | 5/2001 | Ressemann et al. |
| 6,374,476 | B1 | 4/2002 | Ponzi et al. |
| 6,440,062 | B1 | 8/2002 | Ouchi |
| 6,485,455 | B1 | 11/2002 | Thompson et al. |
| 6,530,897 | B2 | 3/2003 | Nardeo |
| 6,579,278 | B1 | 6/2003 | Bencini |
| 6,648,875 | B2 | 11/2003 | Simpson et al. |
| 6,652,506 | B2 | 11/2003 | Bowe et al. |
| 7,008,401 | B2 | 3/2006 | Thompson et al. |
| 7,025,759 | B2 | 4/2006 | Muller |
| 7,101,362 | B2* | 9/2006 | Vanney ............... A61B 18/1492 600/152 |
| 7,269,453 | B2 | 9/2007 | Mogul |
| 7,331,958 | B2 | 2/2008 | Falwell et al. |
| 7,377,906 | B2 | 5/2008 | Selkee |
| 7,591,799 | B2 | 9/2009 | Selkee |
| 7,666,204 | B2 | 2/2010 | Thornton et al. |
| 7,931,616 | B2 | 4/2011 | Selkee |
| 8,298,177 | B2 | 10/2012 | Selkee |
| 2001/0025134 | A1 | 9/2001 | Bon et al. |
| 2001/0027310 | A1* | 10/2001 | Parisi ............... A61L 29/12 604/524 |
| 2001/0037084 | A1* | 11/2001 | Nardeo ............ A61M 25/0138 604/95.04 |
| 2002/0082584 | A1 | 6/2002 | Rosenman et al. |
| 2002/0165461 | A1 | 11/2002 | Hayzelden et al. |
| 2002/0169377 | A1* | 11/2002 | Khairkhahan ... A61B 17/32075 600/433 |
| 2002/0177766 | A1 | 11/2002 | Mogul |
| 2003/0135199 | A1* | 7/2003 | Rosenman ........ A61M 25/0138 604/528 |
| 2004/0193032 | A1 | 9/2004 | Mogul |
| 2005/0021003 | A1* | 1/2005 | Caso ................ A61M 25/0152 604/528 |
| 2005/0097737 | A1 | 5/2005 | Webster, Jr. et al. |
| 2005/0277874 | A1 | 12/2005 | Selkee |
| 2005/0277875 | A1* | 12/2005 | Selkee ............... A61M 25/005 604/95.04 |
| 2006/0184107 | A1 | 8/2006 | Bencini et al. |
| 2007/0100235 | A1 | 5/2007 | Kennedy, II |
| 2007/0232858 | A1 | 10/2007 | Macnamara et al. |
| 2008/0009791 | A1 | 1/2008 | Cohen et al. |
| 2008/0065011 | A1 | 3/2008 | Marchand et al. |
| 2008/0103520 | A1 | 5/2008 | Selkee |
| 2008/0300462 | A1 | 12/2008 | Intoccia et al. |
| 2008/0319420 | A1 | 12/2008 | Rosenman et al. |
| 2009/0234280 | A1 | 9/2009 | Tah et al. |
| 2010/0168827 | A1 | 7/2010 | Schultz |

FOREIGN PATENT DOCUMENTS

| | | |
|---|---|---|
| EP | 1607119 A1 | 12/2005 |
| WO | WO9426347 A1 | 11/1994 |
| WO | WO2008150767 A2 | 12/2008 |

OTHER PUBLICATIONS

JP Office action dated Aug. 14, 2014 issued in JP Application No. 2009-296999, with English translation, 4 pages.

European Patent Office action dated Mar. 19, 2012, issued in EP Application No. 09252919.7, 6 pages.

European Patent Office Search Report dated Jul. 15, 2010, issued in EP Application No. 09252919.7.

European Patent Office Search Report dated Dec. 8, 2009, issued in EP Application No. 09170033.6, 7 pages.

European Search Report and Annex to European Search Report dated Jul. 15, 2010, issued in EP Application No. 09252919.7, 10 pages.

\* cited by examiner

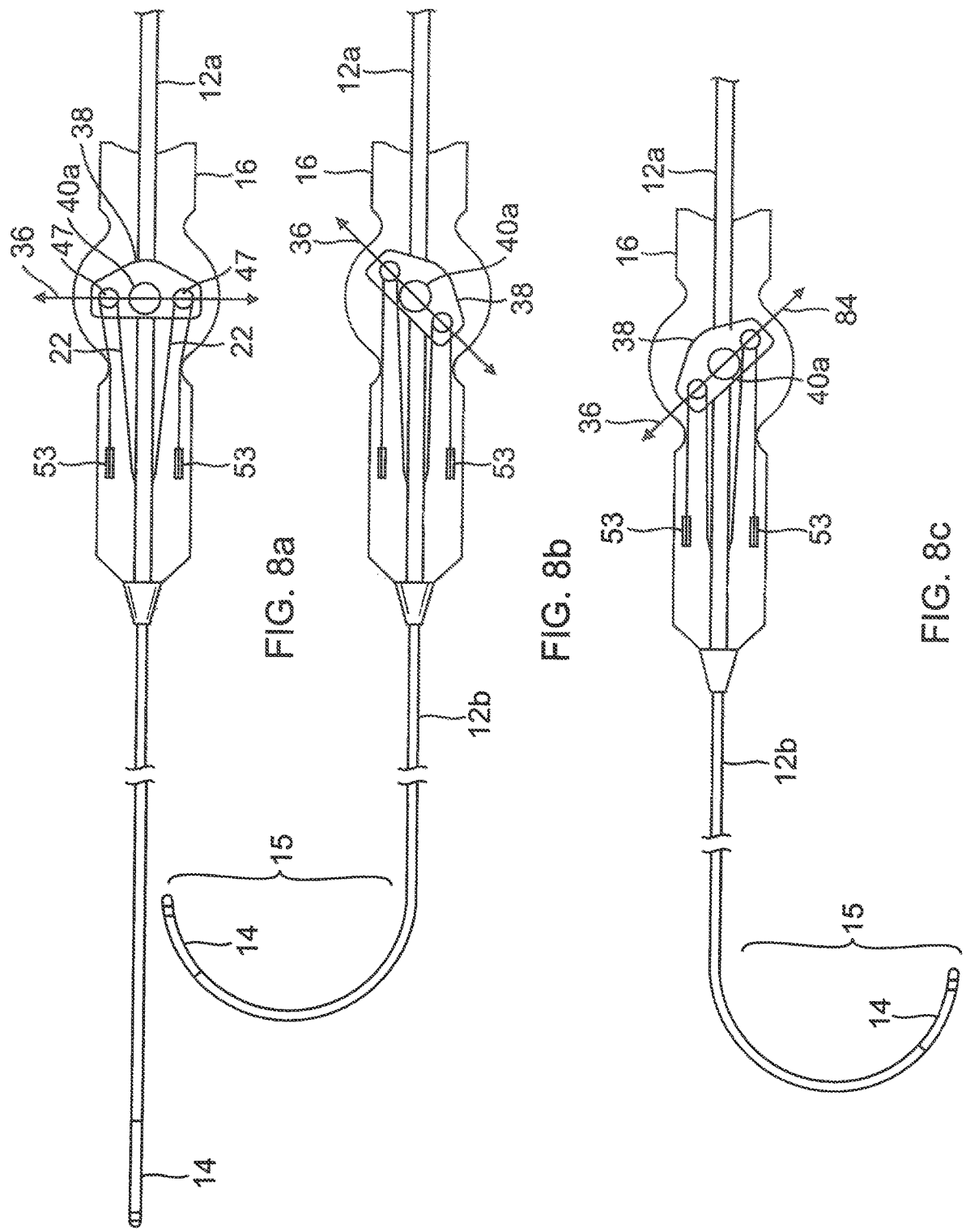

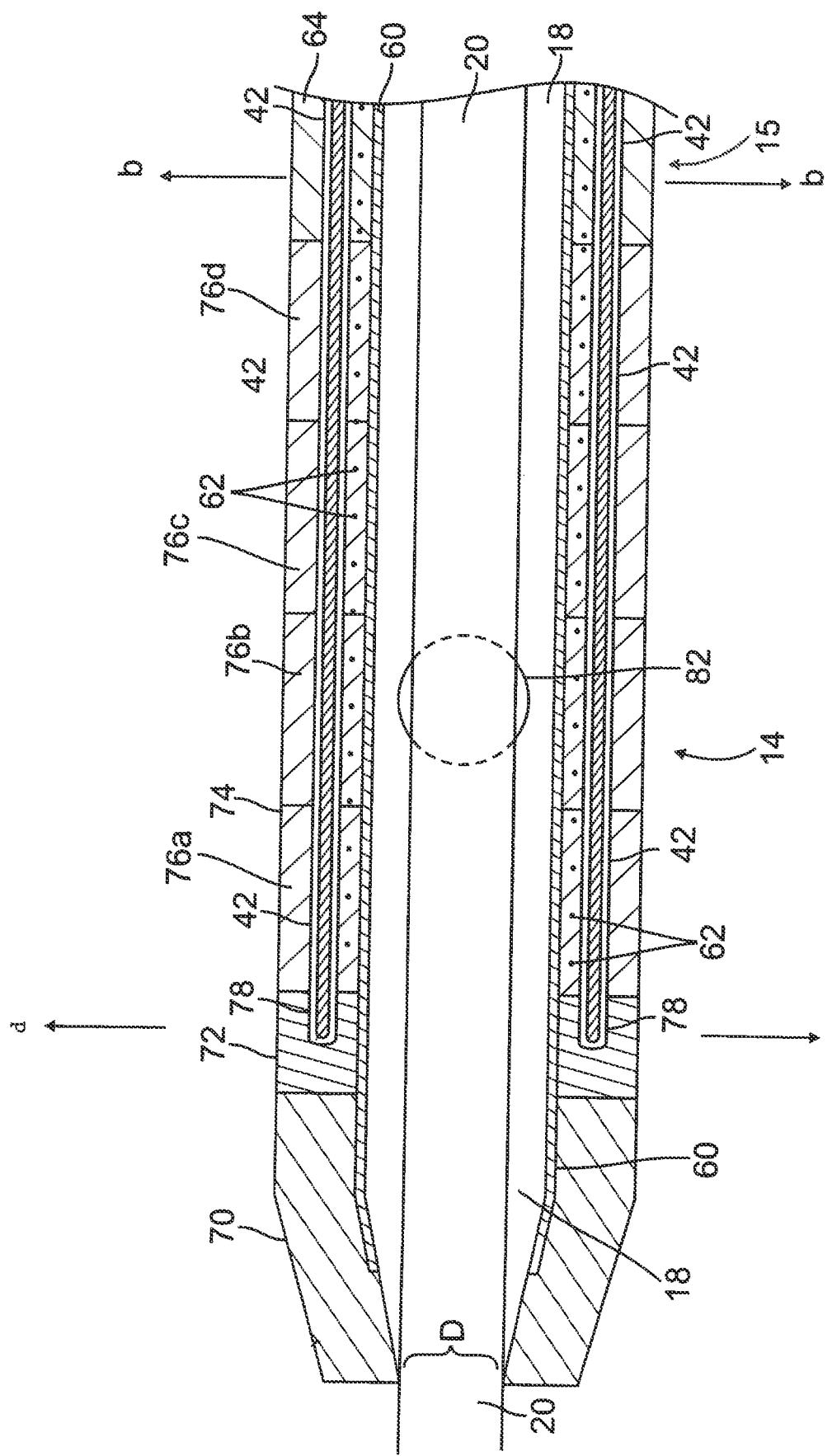

DEFLECTABLE SHEATH INTRODUCER

CROSS-REFERENCE TO RELATED APPLICATION(S)

This application is a continuation of and claims priority to and the benefit of U.S. application Ser. No. 12/346,834 filed Dec. 30, 2008, now U.S. Pat. No. 10,046,141, the entire content of which is incorporated herein by reference.

FIELD OF INVENTION

The present invention relates to sheath introducers for use with catheters, and in particular, deflectable sheath introducers with control handles.

BACKGROUND OF INVENTION

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

The Seldinger technique is a medical procedure for insertion of heart catheters including central venous catheters. It is named after Dr. Sven-Ivar Seldinger (1921-1998), a Swedish radiologist. The technique involves puncturing the vein and inserting a guiding sheath, a guidewire and a dilator into the patient, as is generally known in the art. The dilator is removed, and a catheter is introduced through the guiding sheath whereby a guidewire lumen in the catheter allows the catheter to pass over the guidewire. The guidewire is then removed. For devices not having a guidewire lumen, the guidewire is removed prior to insertion of the device to allow passage. Once the distal end of the catheter reaches the desired location, the guiding sheath is withdrawn to expose the distal end of the catheter which may comprise an electrode assembly for mapping and/or ablation and any other structures to stabilize the electrode assembly in the heart or against the heart wall and tissue. Fluoroscopy may be used to confirm the position of the catheter and to maneuver it to the desired location. Injection of radiocontrast may be used to visualize organs. The sheath may be used for both right-sided procedures, and transseptal electrophysiologic procedures that require puncturing of the septum.

Bidirectional catheters have been designed to be deflectable in one direction by one puller wire and in the opposite direction within the same plane by a second puller wire. In such a construction, the puller wires extend into opposing off-axis lumens within the tip section of the catheter. So that the tip section can bend in both directions in the same plane, the puller wires and their associated lumens are located along a diameter of the tip section. Such catheters typically have a control handle at their distal end which have a thumb knob and/or a rotatable grip that is manipulated by an electrophysiologist to position catheter distal end at the desired location and/or operate electrode assemblies, such as contraction, expansion, deployment, retraction, etc.

Deflectable sheaths are also known, however, the deflection mechanism rotates around the axis of the control handle which facilitates two-handed manipulation but is not ideal for single-handed deflection. Thus, the operator cannot simultaneously deflect the sheath and the catheter extending through the sheath. Existing sheaths also use a soft distal tip with an embedded marker band which does not allow for optimal visualization of the most distal tip and does not provide extensive tip flexibility. Moreover, existing sheaths utilize a consistent cross-sectional profile along the longitudinal axis of the deflectable section which does not allow for changing of stiffness properties near the distal end.

Accordingly, it is desirable to provide a sheath introducer that has bidirectional deflection and a control handle that allows an operator to manipulate with one hand so he can simultaneously operate the control handle of the catheter extending through the sheath introducer. It is also desirable to provide a shaft, and more specifically a deflectable section of the sheath introducer, with sections of different durometer so that flexibility and softness varies near the distal end of the shaft, and in particular, with increased flexibility and softness toward the distal tip of the shaft. It is further desirable that the distal tip be radiopaque for optimal visualization and that the distal tip forms a seal with the catheter or device extending through the shaft so that minimal force is used during punctures and risk of distal tip prolapsing is reduced.

SUMMARY OF THE INVENTION

The present invention is directed to a deflectable sheath introducer having a shaft through which a catheter, needle or device can extend, and a control handle incorporating a deflection assembly that an operator can manipulate for deflecting a deflectable region near a distal section of the shaft, wherein the deflection assembly has a deflection member, a rotatable rocker member and at least a pulley that is engaged with a portion of a tensile member. Rotation of the deflection member about an axis generally perpendicular to a longitudinal axis of the control handle draws on the tensile member to deflect the shaft.

In one embodiment, the introducer has a shaft with a central lumen, a control handle with a deflection assembly, and tensile members each with a distal portion extending along opposing sides of within the shaft and a proximal portion extending within the control handle. The deflection assembly has a deflection arm, and a rocker member rotationally coupled to the deflection arm, wherein the rocker member has at least two pulleys, each engaged with a respective proximal tensile member portion. Rotation of the deflection arm in one direction draws one proximal tensile member portion for deflecting the shaft in the one direction, and rotation of the deflection member in an opposite direction draws the other proximal tensile member portion for deflecting the shaft in the opposite direction.

In more detailed embodiments, the tensile member has a distal puller wire portion and a proximal fiber portion, and the deflection assembly includes a tension knob for adjusting tension of the deflection member. The shaft extends through the rocker member which has cutout so that the rocker member can rotate without interference from the shaft. The shaft may include a softer and more flexible distal section, with a distal tip of a conical cross-section that forms a fluid-tight seal with the device being guided by the introducer. The shaft is formed with opposing off-axis channels for passing the tensile member along the length of the shaft distal of the control handle. With in the control handle, the tensile member is generally outside of the shaft so it can engage with a pulley of the deflection assembly. At the distal section of the shaft, the tensile member may pass radially across a ring attachment for anchoring the tensile member in the distal section.

BRIEF DESCRIPTION OF THE DRAWINGS

These and other features and advantages of the present invention will be better understood by reference to the following detailed description when considered in conjunction with the accompanying drawings wherein:

FIGS. 8a-c show an embodiment of a control handle with its deflection assembly in a neutral position, deflection to the right and deflection to the left.

FIG. 9f is a side cross sectional view of an alternate embodiment of a distal section of a shaft of the present invention.

DETAILED DESCRIPTION OF THE INVENTION

Figure 1:
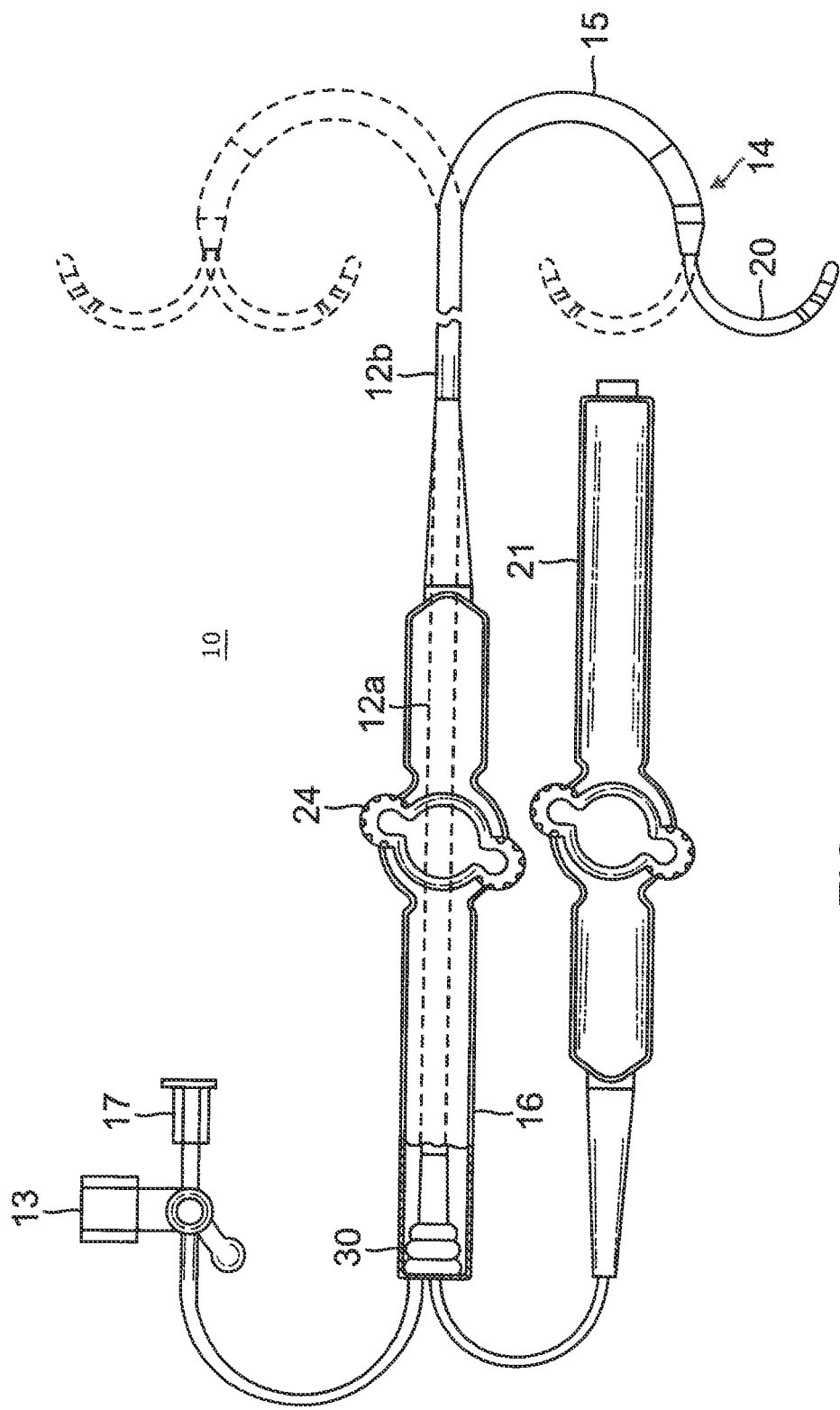
FIG. 1 is a top view of an embodiment of the sheath introducer of the present invention for use with a device inserted therethrough.
Figure 2:
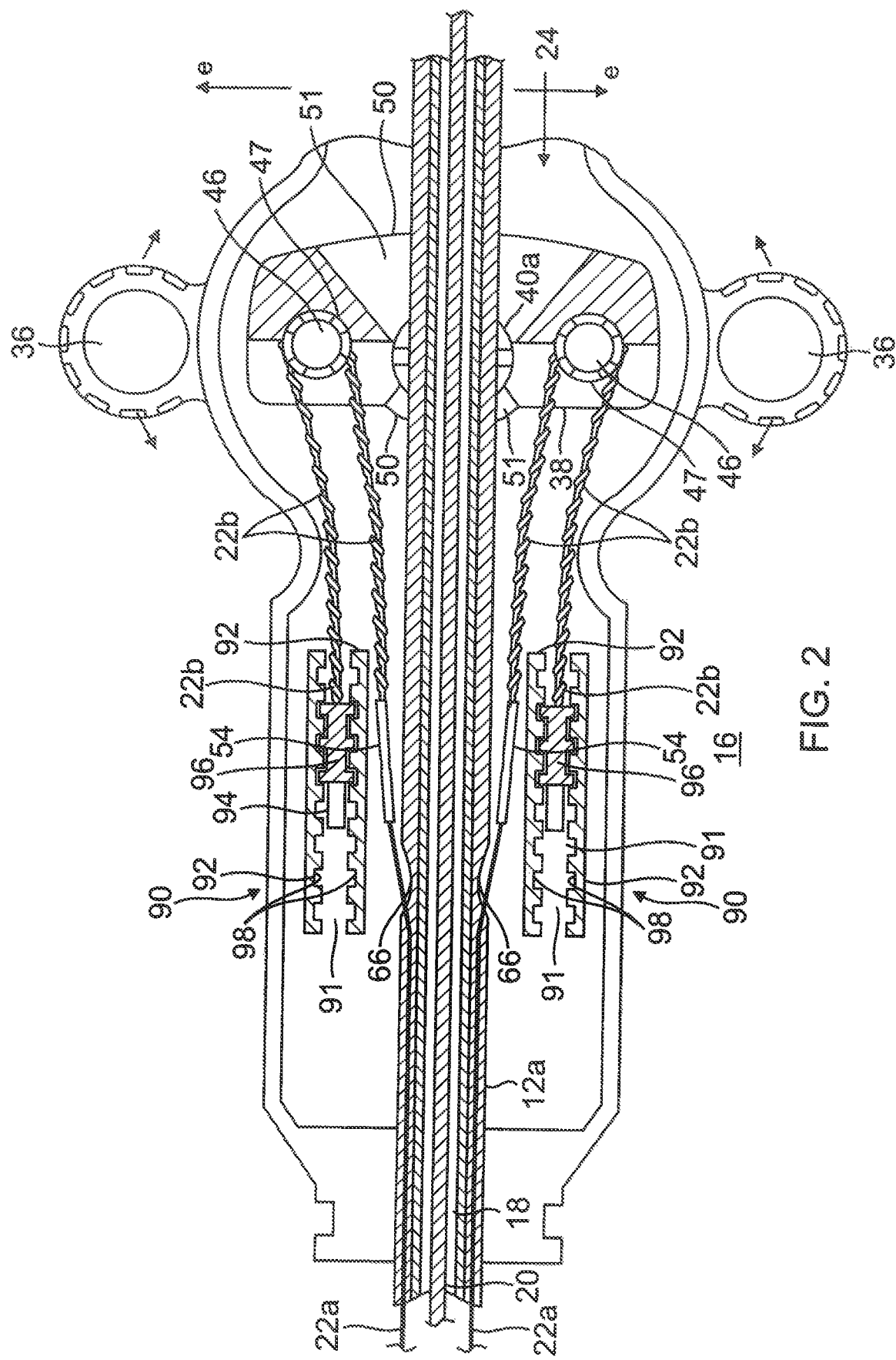
FIG. 2 is top view of an interior of an embodiment of a control handle with a deflection assembly.

FIGS. 1 and 2 illustrate an embodiment a steerable bidirectional sheath introducer 10 for use with a catheter, needle or other device 20 (used interchangeably herein) to be extended through the introducer 10 for entry into a patient's body. The introducer 10 comprises an elongated shaft 12, and a control handle 16 at the proximal end of the shaft 12. Distally, the shaft 12 has a deflectable section 15 and a distal tip section 14. The shaft 12 has a central lumen 18 that extends its entire length for passage of the catheter or other device 20. The shaft 12 extends both distally of the control handle 16 and proximally through the control handle.

For deflecting the deflectable section 15 of the shaft 12, tensile members 22 are provided, with their distal ends anchored at or near the distal tip section 14 and their proximal ends anchored in the control handle 16. Longitudinal movement of the tensile members relative to the shaft 12, which results in deflection of the deflectable section 15, is accomplished by means of the control handle 16 and its deflection assembly 24.

Figure 3:
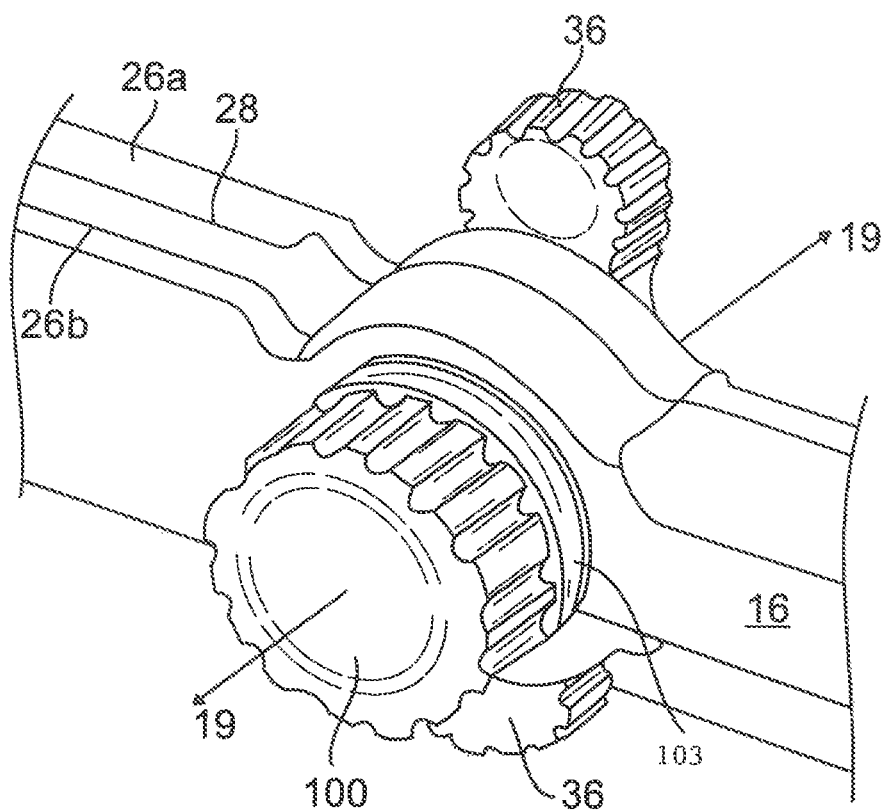
FIG. 3 is a perspective view of an embodiment of a control handle with a tension knob and a deflection member.

With reference to FIGS. 1-3, the control handle 16 comprises a generally elongated handle housing, which can be made of any suitable rigid material, such as plastic configured through a suitable molding process. In the illustrated embodiment, the housing includes two opposing halves 26a and 26b that generally mirror each other and are joined by glue, sonic welding or other suitable means along a longitudinal peripheral seam 28 around the housing. The shaft 12 enters the control handle 16 at its distal end (FIG. 2), extends along the longitudinal axis of the control handle 16 and terminates at the proximal end of the control handle in a hemostatis valve 30 (FIG. 1) that has been integrated into the housing of the control handle. The hemostatis valve forms a fluid tight seal with the device 20 for various purposes, including keeping the lumen 18 of the shaft 12 at positive pressure to prevent patient's loss of blood through the introducer 10 and minimizing the introduction of air into the patient's body. Moreover, the hemostatis valve 30 connects to a side port 13 having a luer hub 17 through which a vacuum can be created to remove air from the inner lumen 18 or through which fluids can be flushed into the lumen 18 to prevent blood from clotting.

Figure 4:
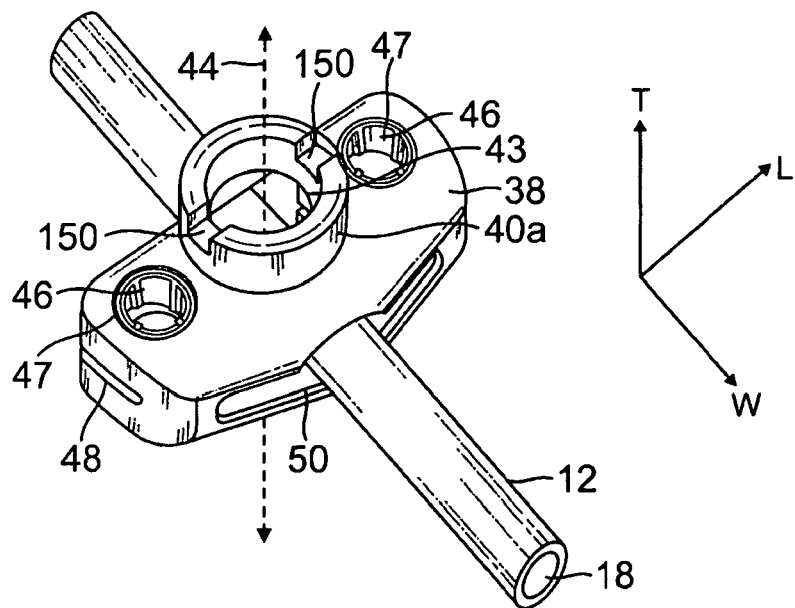
FIG. 4 is a perspective top view of an embodiment of a rotatable rocker member.
Figure 5:
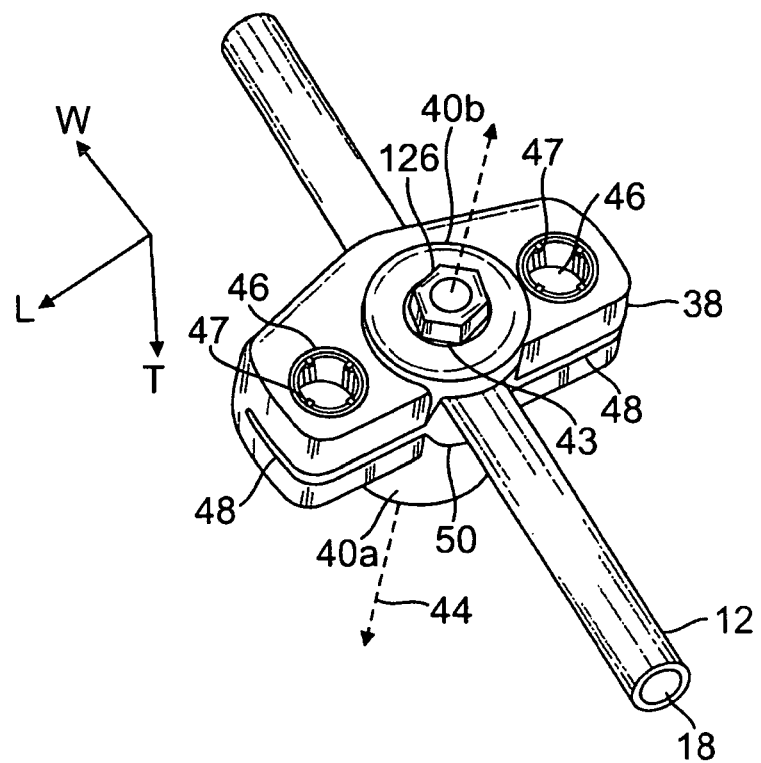
FIG. 5 is a perspective bottom view of an embodiment of a rocker member.
Figure 6:
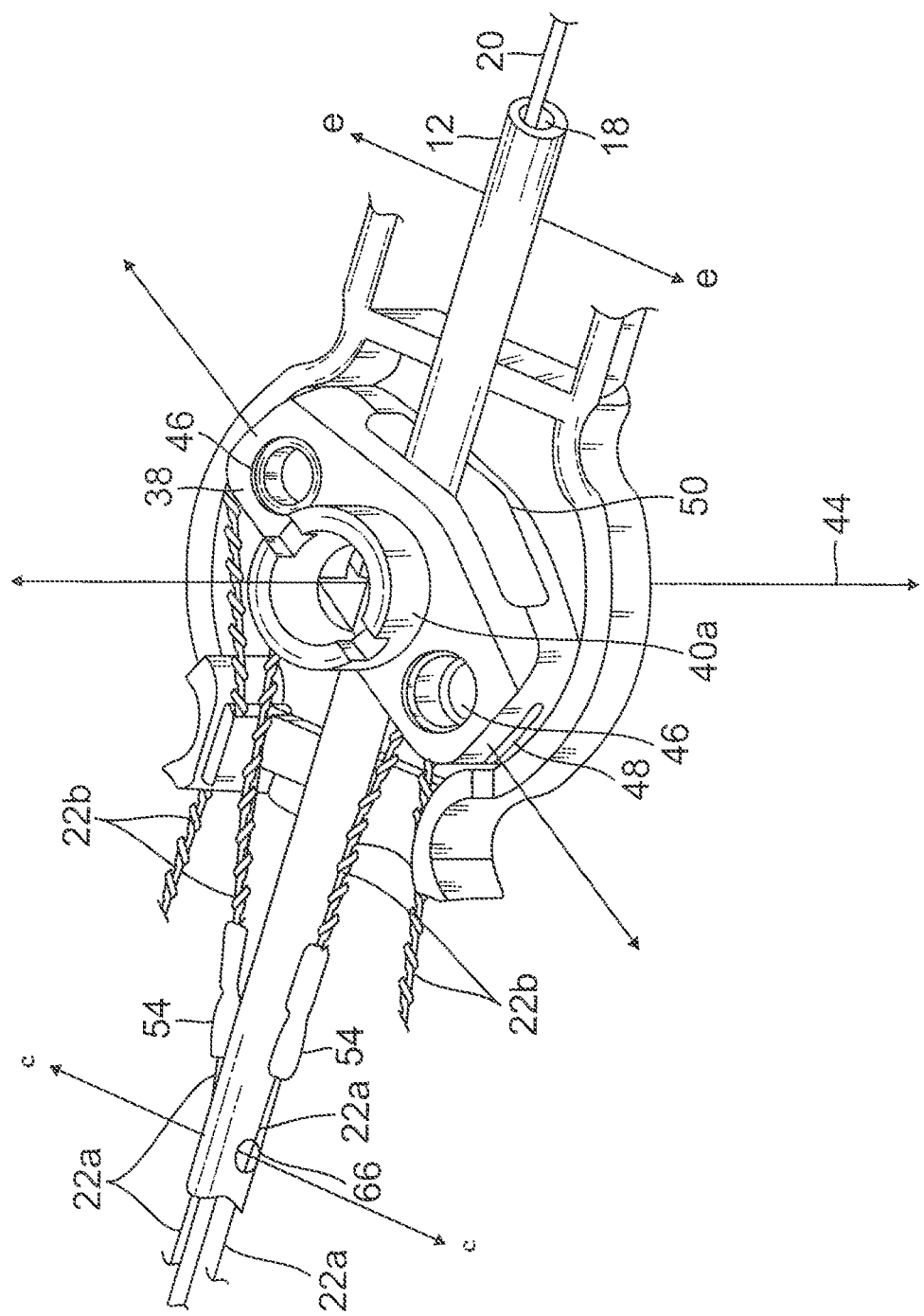
FIG. 6 is a perspective view of an embodiment of an interior of a control handle with a rocker member and tensile members.

The control handle 16 houses components of the deflection assembly 24 (FIG. 3) which includes a deflection member or arm 36 that can be directly manipulated by an operator to control deflection of the shaft 12. The deflection arm 36 is rotatable about an axis 19 that is generally transverse or perpendicular to the longitudinal axis of the control handle. As illustrated in FIGS. 4-6, the deflection assembly 24 has a rotatable rocker member 38 that acts on the tensile puller members 22 to deflect the shaft 12. The rocker member 38 has a length L dimension, a width W dimension and a thickness T dimension.

Figure 7:
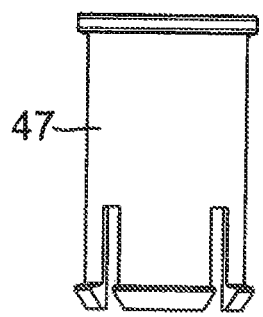
FIG. 7 is a side elevational view of an embodiment of a pulley.

Along its thickness dimension, the rocker member 38 is configured with two opposing annular formations 40a and 40b that define a central hole 43 that extends through the thickness of the member 38. The central hole 43 defines an axis of rotation 44 that is coaxial with rotational axis 19 of the deflection arm 36. Along its length, the rocker member 38 also has two smaller holes 46 that oppose each other from the central hole 43. In each hole sits a pulley 47, for example, a snap bearing (FIG. 7), that has a rotational axis parallel to the rotational axis 19. A tensile member 22 enters the rocker member through slots 48 and a portion is wound around a respective pulley 47.

To accommodate the shaft 12 extending across and through the control handle 16, the rocker member 38 has a channel 50 extending through its width. Distal and proximal portions of the channel 50 have indents, e.g., triangular or wedge-shaped, 51 (FIG. 2) to allow the rocker member 38 to rotate freely within a predetermined range of angles, e.g., about ±45 degrees of the longitudinal axis of the control handle 16, without interference with the shaft 12.

As understood by one of ordinary skill in the art, the rocker member 38 and the pulleys 47 are arranged such that rotation of the rocker member in one direction about the axis 44 draws back one tensile member 22 to deflect the shaft 12 in that direction. With reference to FIGS. 8a-8c, as the rocker member 38 is rotated by means of the deflection arm (as represented by line 36), the pulleys 47 are displaced from a neutral position (FIG. 8a) with one pulley 47 drawing a tensile member 22 on one side of the shaft 12 against its anchored proximal end 53 for deflecting the shaft toward that side (FIGS. 8b and 8c).

Each tensile member 22 may comprise multiple segments. As best illustrated in FIG. 2, each tensile member has a distal puller wire portion 22a and a proximal tensile fiber portion 22b that are joined or connected at a location with in the control handle 16 distal the rocker member 38. The puller wire portions 22a and the tensile fiber portions 22b are connected or secured to each other by a connector 54, e.g., a crimped brass ferrule covered by shrink tubing. The puller wire portions 22a extend nearly the entirety of distal shaft portion 12b distal the control handle. The tensile fiber portions 22b extend inside the control handle 16 generally outside proximal shaft portion 12a. In this manner, it is the more flexible tensile fiber portions 22b that interact with the pulleys 47 and undergo repeated bending and straightening during deflection operations, as they are less prone to bending stress and fatigue failure.

Each puller wire portion or puller wire 22a is made of any suitable metal, such as stainless steel or Nitinol. Preferably each puller wire has a low friction coating, such as a coating of Teflon® or the like. Each puller wire has a diameter preferably ranging from about 0.006 inch to about 0.012 inch. Preferably both of the puller wires have the same diameter. Flat puller wires may be used in place of round puller wires. Their cross sectional dimensions should be such that they provide comparable tensile strengths as round puller wires.

Each tensile fiber portion or tensile fiber 22b may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™) The term fiber is used herein interchangeably with the term fibers in that the tensile fiber may be of a woven or braided construction. In any case, these materials tend to be flexible, providing suitable durability when used in wrapped engagement with the pulleys and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions.

In the illustrated embodiment of FIGS. 9a-9e, the shaft 12 comprises an elongated tubular construction having a single, axial or central lumen 18, and two considerably smaller off-axis channels or lumens 42, one on each side of the central lumen 18 along a diameter of the shaft 12. Each channel 42 may be lined by a compression coil or stiffener 41 (FIG. 9b) from the proximal end of the shaft 12 at the hemostatis valve 30 inside the control handle 16 to a proximal end of the deflectable section 15 (FIG. 1) to resist buckling during deflection of the deflectable section 15. Lining the lumen 18 of the shaft 12 is an inner layer or lining 60 (e.g., of PTFE or TEFLON®) which reduces friction and enhances smooth passage of a catheter or device through the shaft. The lining 60 is surrounded by a braided mesh 62 of stainless steel or the like that is covered by an outer layer body 64. The braided mesh 62 increases the torsional stiffness of the shaft 12 so that when the control handle 16 is rotated the distal end of the shaft 12 will rotate in a corresponding manner. The outer layer 64 may be made of a suitable polymer, such as polyurethane or PEBAX® (polyether block amide). If extruded, the outer layer 64 can better bond the braided mesh 62 to the lining 60. For an 8 french sheath introducer, the outer diameter of the shaft 12 is preferably no more than about 12.5 french, more preferably about 11.5 french. The inner diameter or central lumen 18 of the shaft is preferably no less than about 8 french, more preferably between about 8.25 and 8.5 french. The off-axis channels 42 may be formed in the outer layer 64 during extrusion or molding for shafts manufactured with such processes. The channels 42 may also be formed by means of a round or flat tube (of PTFE or other suitable material) during lamination of the outer layer. It is understood by one of ordinary skill in the art that the material, shape and size of the tube may vary to accommodate various tensile member designs and materials.

Figure 9A:
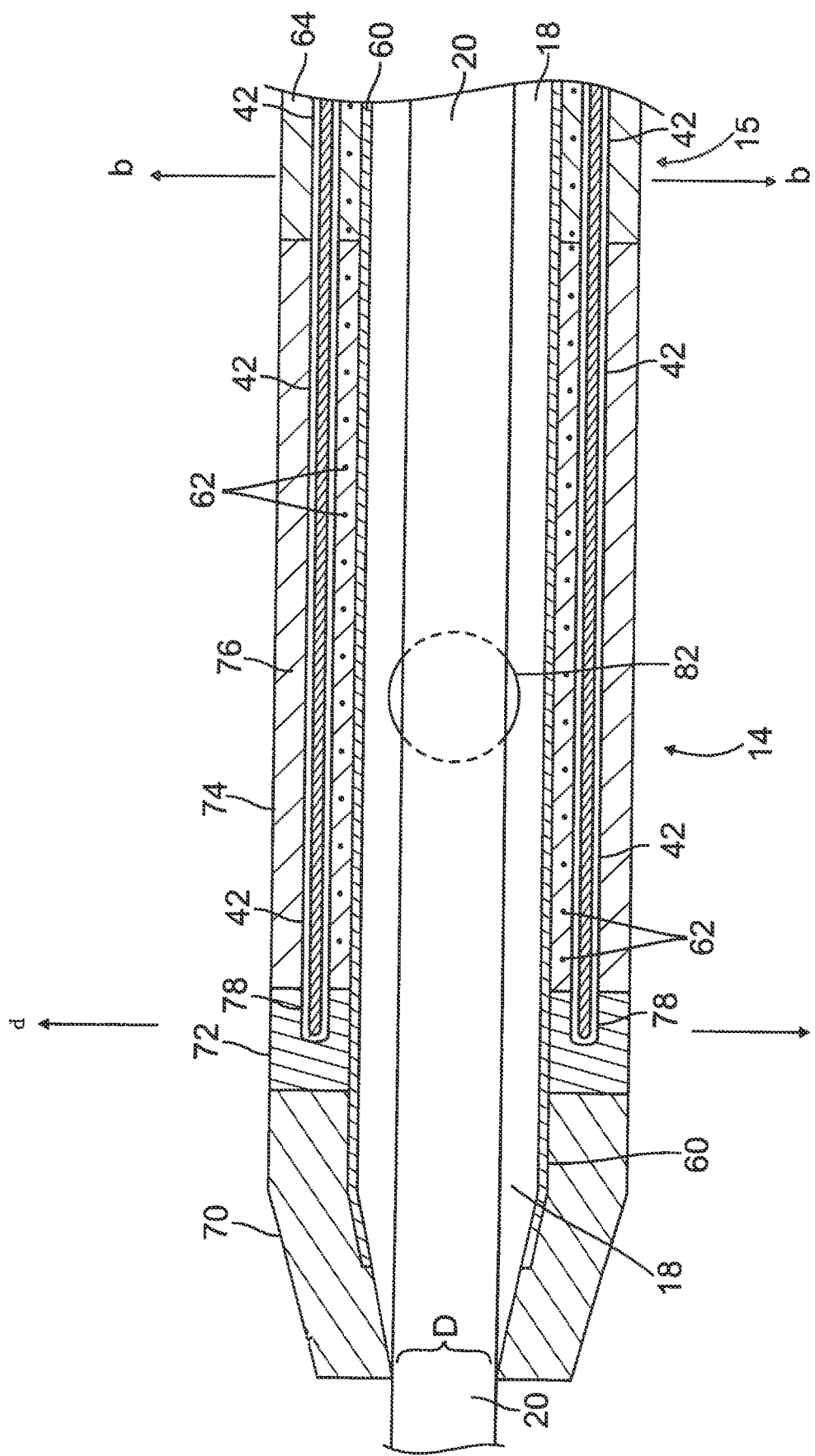
FIG. 9a is a side cross sectional view of an embodiment of a distal section of a shaft of the introducer 10.
Figure 9B:
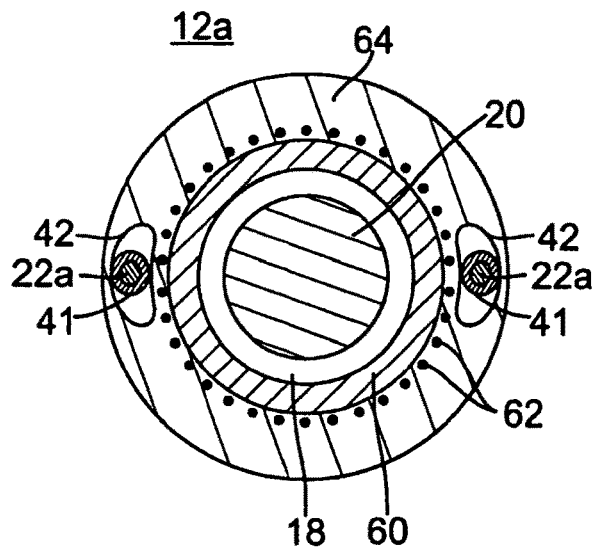
FIG. 9b is a longitudinal cross sectional view the distal section of FIG. 9a, taken along line b-b.
Figure 9C:
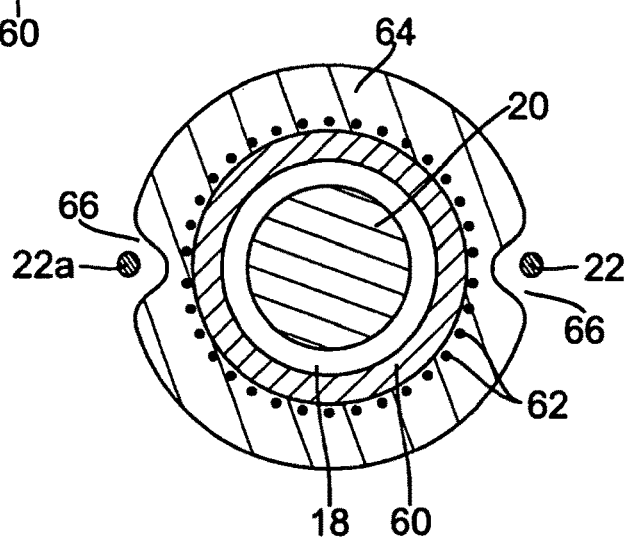
FIG. 9c is a longitudinal cross sectional view of the distal section of FIG. 9a, taking along line c-c.
Figure 9D:
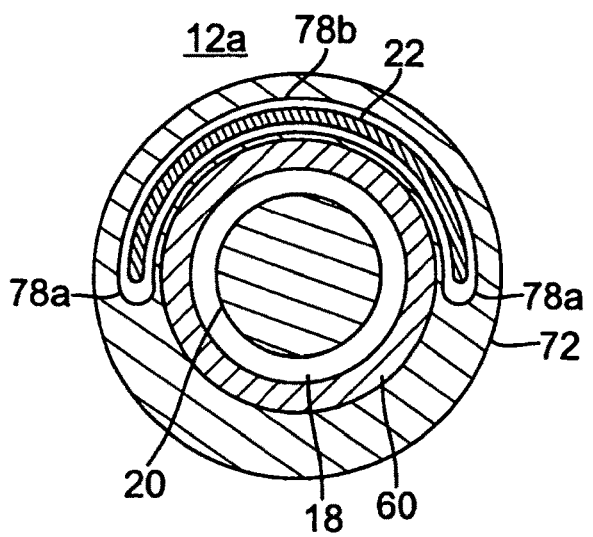
FIG. 9d is a longitudinal cross sectional view of the shaft of FIG. 8, taken along line d-d.
Figure 9E:
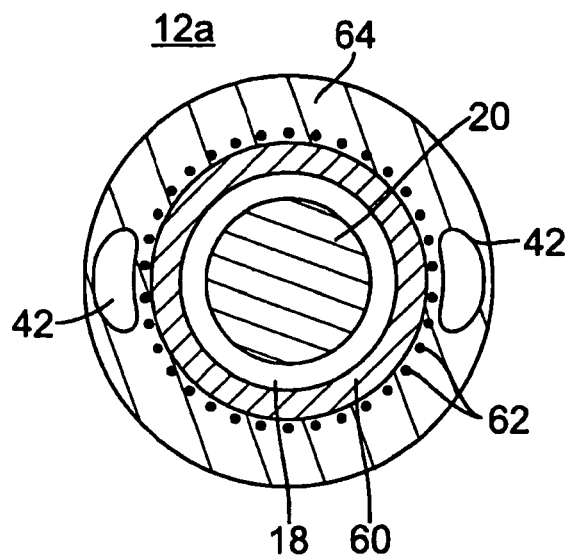
FIG. 9e is a longitudinal cross sectional view of the shaft of FIG. 2, taken along line e-e.

With reference to FIGS. 6 and 9c, a port or opening 66 is cut or otherwise provided at a location along the proximal shaft portion 12a extending within the control handle 16 to allow the tensile members 22 to enter the off-axis channels 42. In the illustrated embodiment, the distal puller wire portions 22a of the tensile member passes into the openings 66 and extend distally into the channels 42 of the shaft.

Distally, the shaft 12 includes a distal tip section 14 distal of the deflectable section 15. The distal tip section comprises a conical tip 70, a fastener, e.g., a ring attachment 72, for the tensile member and a transition portion 74 that bridges the deflectable section 15 and the conical tip 70. The conical tip can be made of a soft, radiopaque material. The central lumen 18 extends through the distal tip section 14. Although the outer layer 64 of the shaft terminates at the proximal end of the distal section 14, the lining 60 and the braided mesh 62 of the shaft 12 extend into the transition portion 74 and are covered by an outer layer 76. In the disclosed embodiment, the outer layer 76 has a different durometer than the outer layer 64 so that the transition portion 74 can be softer and more flexible than the shaft 12. For example, the outer layer 76 can be a softer and more flexible cannula material. As illustrated, the off-axis channels 42 continue extend through the outer layer 76. Furthermore, the outer layer 76 of the transition portion 74 may be comprised of multiple sections 76a-76d of materials with different durometers to provide a change in flexibility of the deflectable region 15 relative to location from the conical tip 70 (FIG. 9f)

The lining 60 extends from the transition segment 74, through the attachment ring 72 and terminates in the conical tip 70. The portion of the lumen 18 in the conical tip 70 tapers accordingly with the conical profile of the tip 70, with a diameter D of the lumen 18 at a distal end being sufficient to allow passage of the device 20 while forming a circumferential fluid-tight seal against the device. To that end, the material of the conical tip 70 is elastic to facilitate the formation of the seal. Ports 82 are provided in the transition segment 74 through the lining 60, the braided mesh 62 and the outer layer 76 so that fluid can escape from the central lumen 18 to prevent the formation of a vacuum as the device 20 moves therethrough.

Between the conical tip 70 and the distal end of the transition portion 74, the attachment ring 72 serves as an anchor for the tensile members extending through the off-axis channels 42. With reference to FIG. 9c, the tensile members 22a emerging from each off axis channel 42 extend through a passage 78 formed in the attachment ring 72 that includes radial passages 78a that are aligned with the off-axis channels 42 and a circumferential passage 78b linking the radial passages. In this case, it is understood that the tensile members 22a is a continuous structure that extends from one channel 42 into the other channel 42. Bonding between the tensile members 22a and the ring 72 prevents the tensile members 22a from moving or dislocating. The ring 72 can be made of a material similar to that of the conical tip 70 and/or the transition segment outer layer 76, with similar melt temperatures. The ring 72 may be formed by lamination or molding. Interfacing edges or junctions within the distal section 14, between the conical tip 70, the ring 72 and the transitional portion 74 can be joined by thermal bonding, and/or glue or adhesives.

The attachment ring 72 anchors the tensile member 22 so that as a proximal end of the tensile member is drawn proximally by a pulley 47 of the rocker member 38 of the deflection assembly 24, the shaft 12 is deflected toward that tensile member (FIGS. 8b and 8c).

Figure 10A:
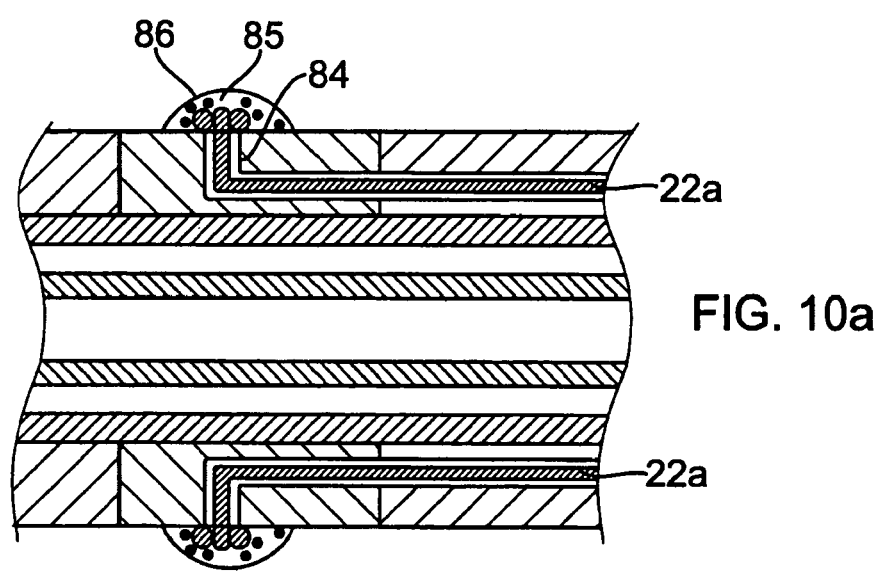
FIG. 10a is a side cross sectional view of an alternate embodiment of a distal tip section of a shaft.
Figure 10B:
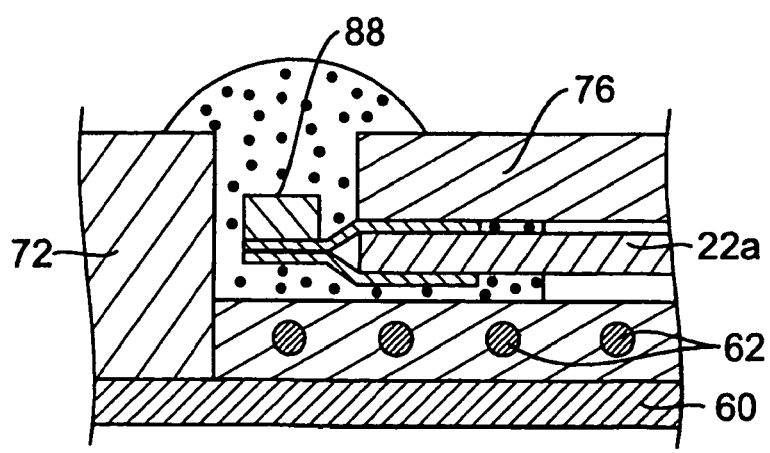
FIG. 10b is a side cross sectional view of another alternate embodiment of a distal tip section of a shaft.

Alternatively, the tensile member 22 can pass through holes 84 formed in the transition segment ring 72 and be wrapped around the outer surface for several windings 85 and be affixed to the outer surface by lamination 86 (FIG. 10a). As another alternate embodiment, the distal ends of the tensile member can be anchored to the side wall of the shaft 12 by means of a T-bar anchor 88 (FIG. 10b) as known in the art. Of course, in this case, the tensile members need not be connected or joined in the distal section of the shaft 12. Other means for anchoring the tensile members 22 (as either a continuous member or separate members) at or near the tip section 14 would be recognized by those skilled in the art and are included within the scope of the invention. It is understood that the bi-directional deflection of the deflectable section 15 can be symmetrical or asymmetrical, planar or nonplanar, depending on various factors, including the location of the distal anchor(s) of the tensile member(s) are anchored and the configuration of the off-axis channels 42.

Referring back to FIG. 2, the portions of the tensile members within the control handle 16 are the tensile fiber portions 22b, each of which extends proximally from the connector 54 toward the rocker member 38 where each is wound around a pulley 47 and turns about 180 degrees to double back toward the distal end of the control handle. Each proximal end of the tensile member 22b is anchored by an anchor assembly 90 that includes a pair or racks 92, a slug 94 and a stop 96. The proximal end of the tensile member 22b extends between a respective channel 91 defined by the pair of racks 92, and the proximal end of each tensile fiber is encased within a molded member or slug 94 sized to fit in and to translate in the channel 91. Proximal the slug are the stops 96 that are adjustably positioned in a selected location along the racks 92, for example, by means of interlocking teeth 98 formed in the racks and the stops to releasably lock in the selected position against movement. The stops 96 are formed so that each respective tensile fiber 22b can slide through them, below or around them but the stops 96 block the slugs 94 from moving proximally past them. Accordingly, the stops 96 limit the proximal movement of the slugs 94 and anchor the proximal ends of the tensile fibers 22b to effectuate deflection when each is drawn proximally by the deflection assembly 24. During assembly of the control handle 16 before the two housing halves 26a and 26b are joined, the stops 96 are selectively positioned between the racks 92 to achieve a desirable tension in each tensile member. The interlocking teeth of the racks 92 and stops 96 allow for fine adjustments in setting the tension.

Figure 11:
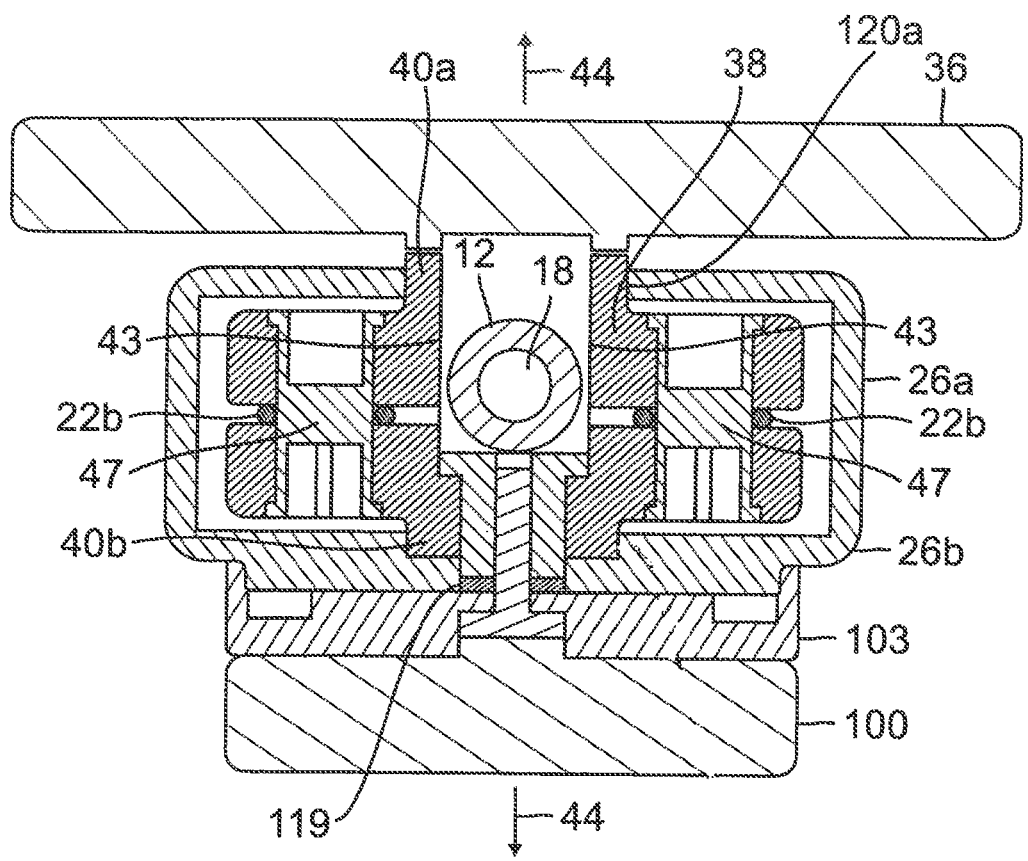
FIG. 11 is a longitudinal cross sectional view of an embodiment of a deflection assembly of the control handle.

With reference to FIGS. 3 and 11, the deflection assembly 24 also includes a rotation tension knob 100 that allows an operator to set the ease with which the deflection arm 36 can be rotated. The construction and assembly of the deflection assembly 24, inclusive of the deflection arm 36 and the tension knob 100, are described as follows.

Figure 11A:
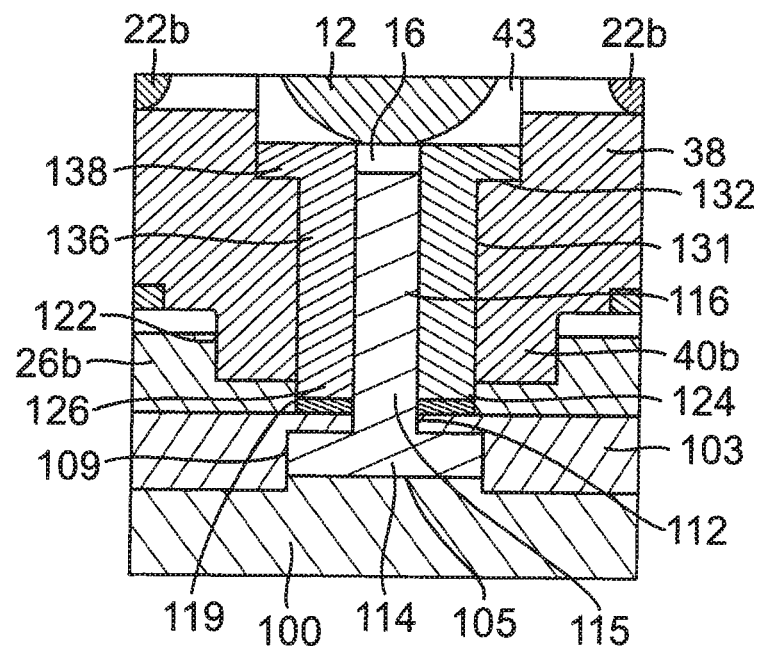
FIG. 11a is a detailed view of a portion of the deflection assembly of FIG. 11, showing a bolt and a retaining nut.
Figure 12:
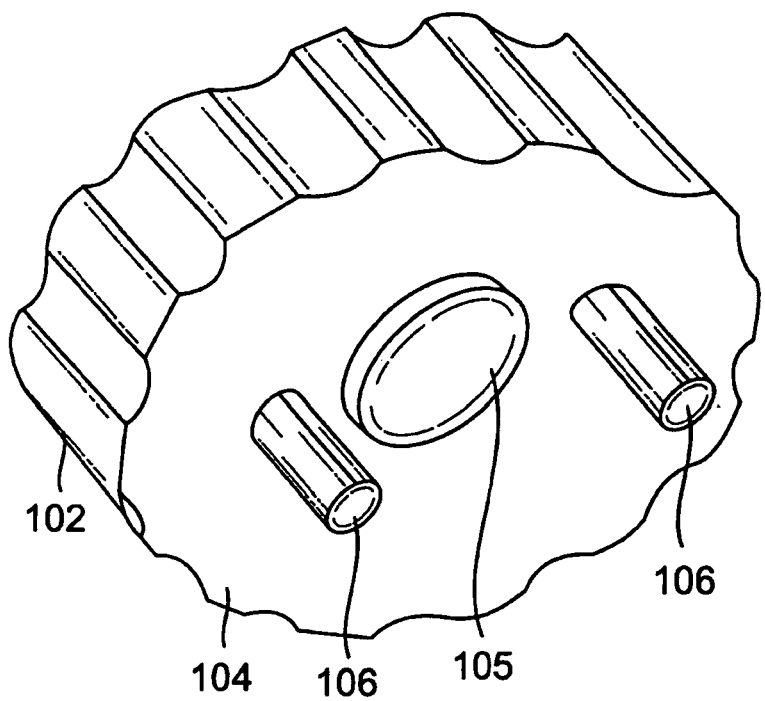
FIG. 12 is a perspective view of an embodiment of a tension knob.
Figure 13:
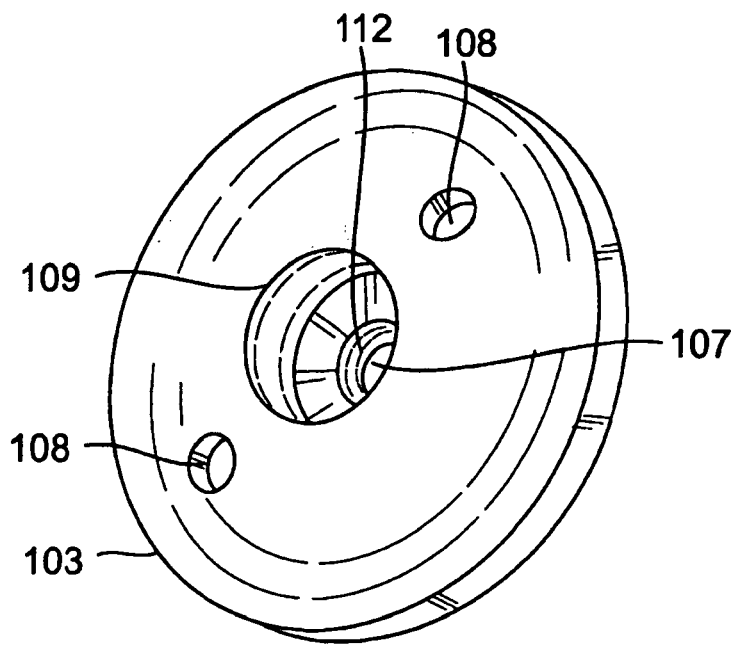
FIG. 13 is a perspective view of an embodiment of a locking plate.
Figure 14:
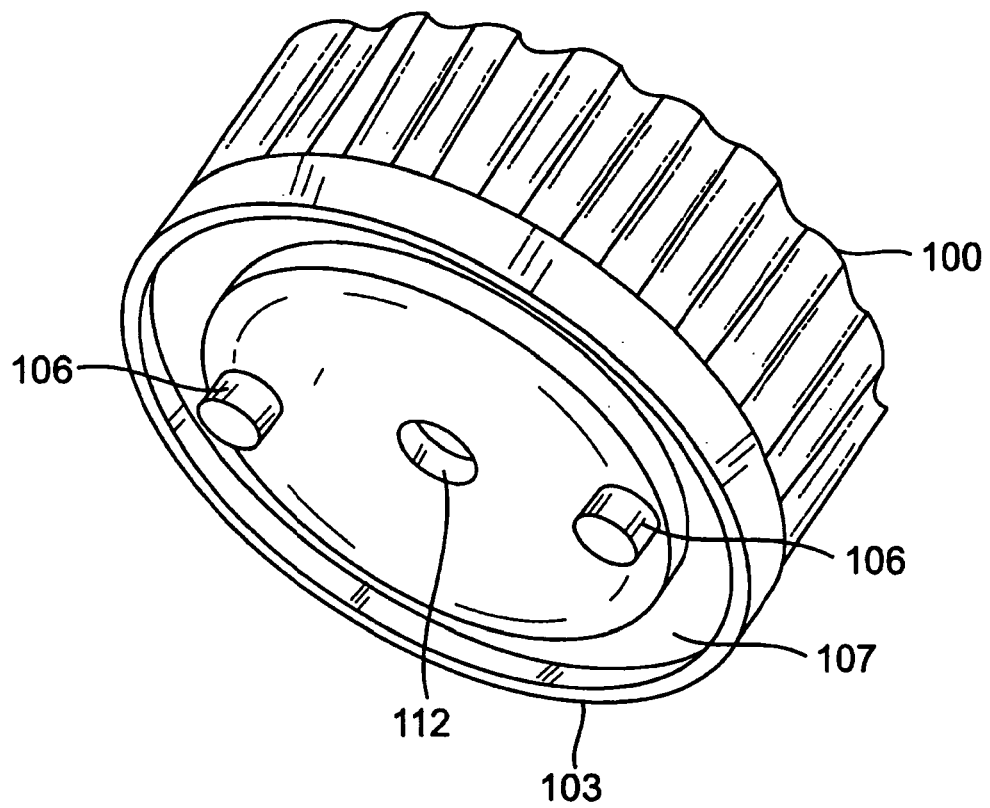
FIG. 14 is a perspective of an embodiment of an assembly including the tension knob and the locking plate.
Figure 15:
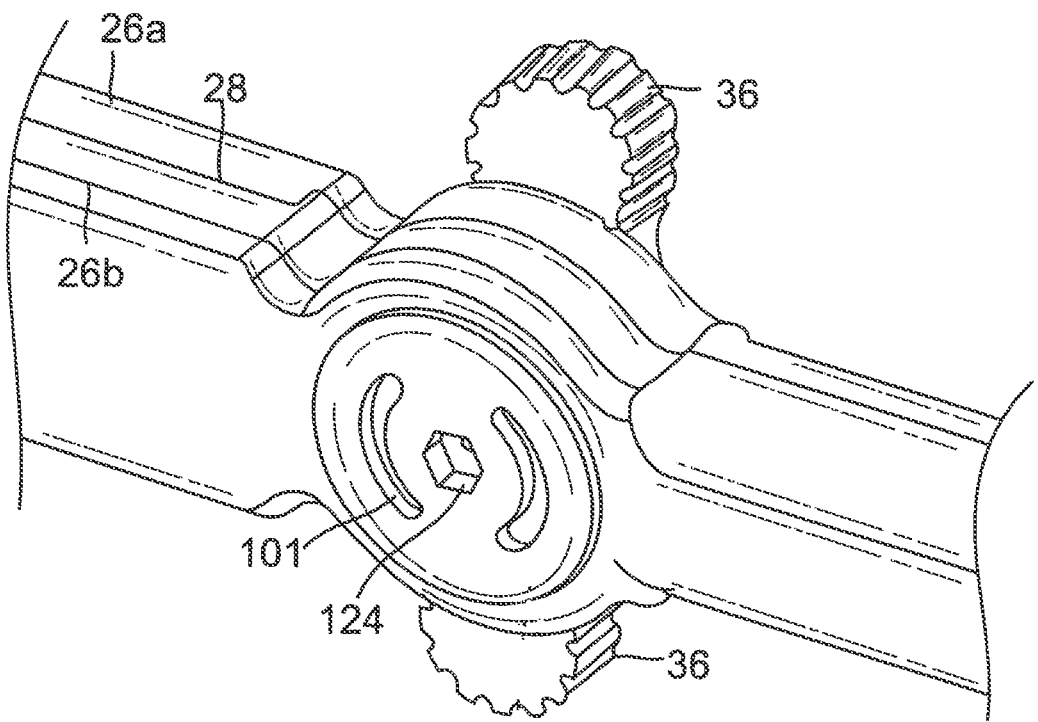
FIG. 15 is a perspective view of an embodiment of a control handle.

With reference to FIGS. 3, 11, and 11a, the deflection arm 36 and the tension knob 100 are mounted opposite of each other with the housing halves 26a and 26b of the control handle 16 therebetween. The tension knob 100 has a generally circular cross section with a circumferential edge 102 having a friction-inducing surface (FIG. 12). A central circular protrusion 105 and two prongs 106 along a diameter project from a surface 104 of the knob 100. A locking plate 103 (FIG. 13) is sandwiched between the knob 100 and the housing half 26b. The locking plates has a central opening 107 and two holes 108. The two prongs 106 of the knob 100 are inserted through the two holes 108 in the plate 103 and extend therethrough to engage semi-circular grooves 101 (FIG. 15) formed in an outer surface of the housing half 26b. The grooves 101 limit the degree of rotation of the knob 100 in clockwise and counterclockwise directions. The central opening 107 of the plate 103 (FIG. 13) has different cross-sections that include a larger circular cross-section 109 and a smaller circular cross-section 112. The larger circular cross-section 109 receives a head 114 of a cap screw-type bolt 115, and the smaller circular cross-section 112 receives a body 116 of the bolt 115. The central protrusion 105 of the tension knob 100 forms a press fit with the head 114 of the bolt 115 to create rotational alignment between these two components. The prongs 106 lock and rotationally couple the tension knob 100 and the lock plate 103, and the bolt 115 is rotationally coupled to the plate 103. Coupling of the tension knob 100 and the locking plate 103 may also be achieved by means of welding the two components together. In that case, the prongs 106 need not protrude from the tension knob but rather from the locking plate 103.

Figure 16:
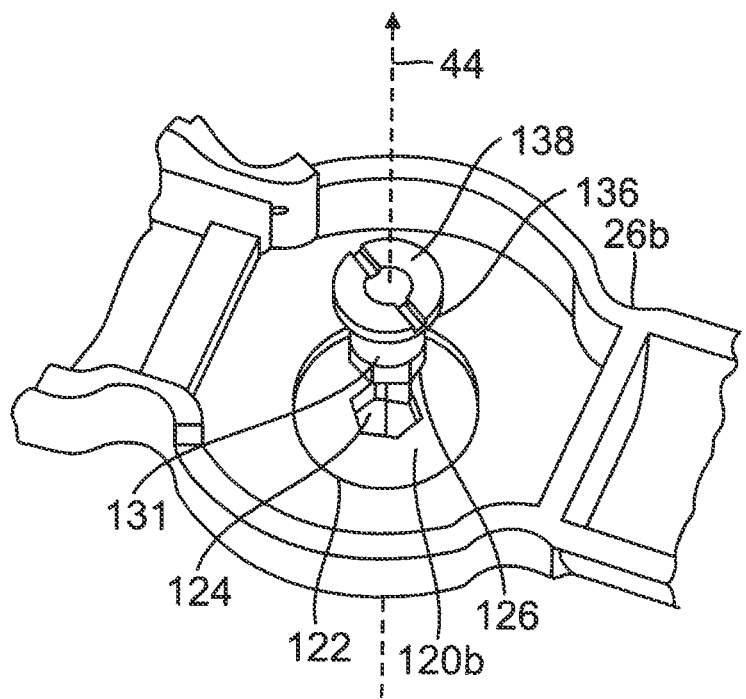
FIG. 16 is a partial perspective view of an embodiment of an interior of one housing half of a control handle.

With reference to FIG. 11, the rocker member 38 is situated between the two halves 26a and 26b of the control handle 16, with each of annular formations 40a and 40b extending respectively through an opening 120a and 120b formed in each housing half. The opening 120b in the housing half 26b (FIG. 16) has a larger circular cross section 122 to receive the annular formation 40b, and a polygonal cross-section 124 to receive a matching polygonal cross-section distal end 126 of a retaining nut 136 whose head 138 abuts a circumferential edge 132 (FIG. 11) formed in the central hole 43 of the rocker member 38. The body 116 of the bolt 115 extending through the plate 103 is received in the retaining nut 136 to join the tension knob 100 to the rocker member 38, with the housing half 26b and a washer 119 (e.g., Belleville type) secured therebetween. The polygonal distal end 126 of the retaining nut 136 rotationally couples the nut 136 and the housing half 26b while a circular body portion 131 (FIG. 16) of the nut 136 allows rotational independence between the nut 136 and the rocker member 38. Thus, rotation of the knob 100 in one direction which turns the bolt 115 to advance into the retaining nut 136 compresses components including the annular formation 40b and the washer 119 against the housing half 26b which tightens the knob 100. Likewise, rotation of the knob 100 in the opposite direction which turns the bolt 115 to withdraw from the nut 136 releases the compression which loosens the knob 100.

Figure 17:
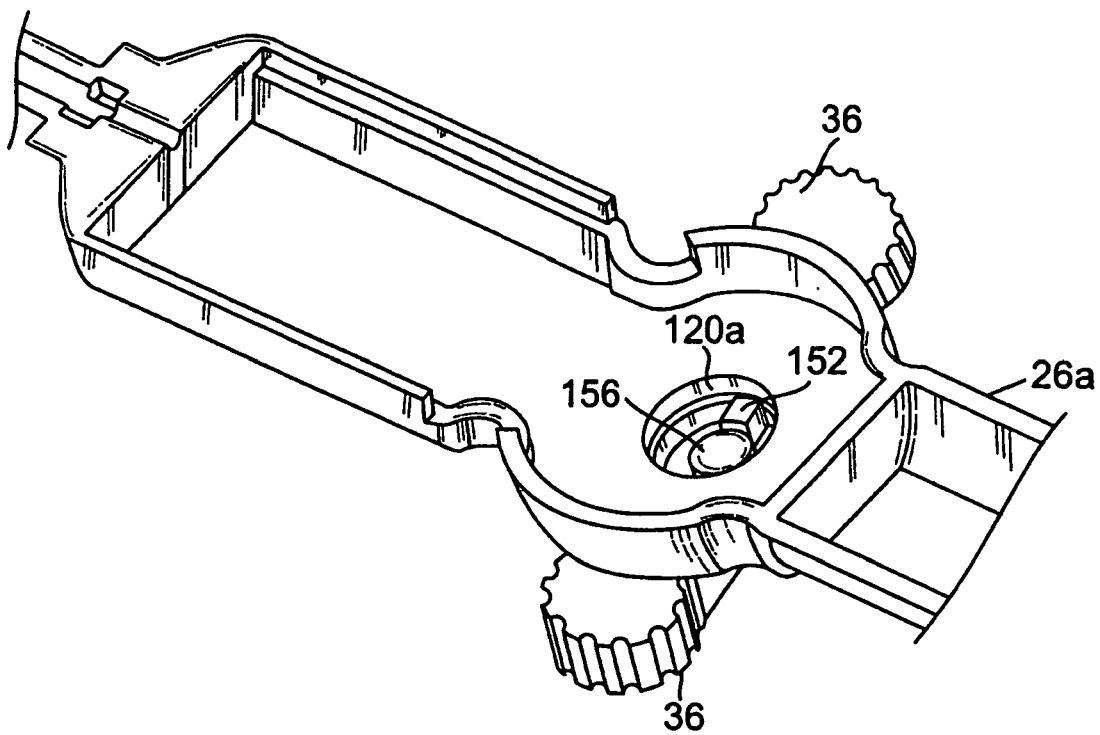
FIG. 17 is a partial perspective view of an embodiment of an interior of another housing half of a control handle.
Figure 18:
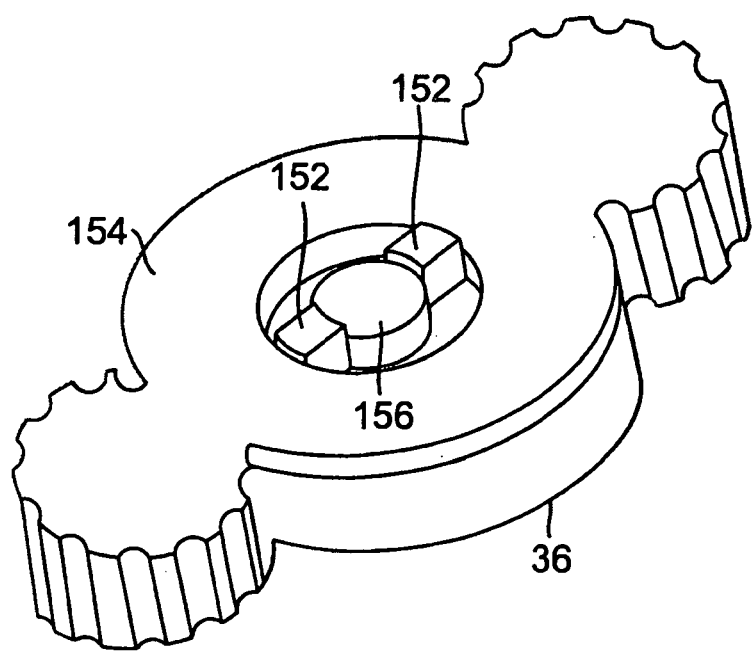
FIG. 18 is a perspective view of an embodiment of a deflection member.

In assembling the deflection arm 36 to the control handle 16, the rocker member 38 is positioned so the annular formation 40a extends through the opening 120a (FIG. 17) in the housing half 26a. The annular formation 40a has recesses 150 (FIG. 4) that lock with protrusions 152 projecting from a facing surface 154 of the deflection arm 36 (FIG. 18), which rotationally couple the deflection arm 36 and the rocker member 38. The protrusions 152 can snap fit into the recesses 150 and/or be secured by adhesives, glue, sonic welding and the like. A central circular protrusion 156 fits into the annular formation 40a of the rocker member 38.

In use, the shaft 12 of the introducer 10 is introduced into a patient's body through an opening in a vein. Through the lumen 18 of the introducer 10, a guidewire is fed, followed by a dilator, as is generally known in the art. The dilator is removed, and the device is introduced through the hemostatis valve 30 at the proximal end of the control handle 16 to enter the central lumen 18 of the introducer 10 whereby the guidewire is passed through a guidewire lumen in the device. For devices not containing a guidewire lumen, the guidewire is removed from the sheath prior to insertion of the device. The luer hub 17 on the side port 13 can be used to draw or inject fluid into the central lumen 18 of the sheath introducer 10 as needed. An electrophysiologist uses one hand to manipulate the control handle 16 of the introducer 10 and his other hand to manipulate the control handle 21 of the device 20. The electrophysiologist can deflect the deflectable region 15 of the shaft 12 with one hand while deflecting an exposed deflectable region of the device 20 with the other hand. The distal section 14 of the deflectable section 15 with its increased flexibility can be used to provide improved positioning capabilities of the device 20. Additionally, the combined stiffness of the device 20 and the shaft 12 provides improved back support for the device 20 and aids in maintaining positioning once the device 20 is in place. The conical tip 70 of the shaft 12 maintains a tight seal with the device 20 so that force is minimized during punctures. Fluid can enter or leave the central lumen 18 of the distal section 14 via ports 82 so that there is no vacuum to prevent the device 20 from moving freely through the central lumen 18 of the shaft 12.

By rotating the deflection arm 36 to one direction, the deflectable section 15 (along with the device 20 therethrough) is deflected in that direction. By rotating the deflection arm 36 to the other direction, the deflectable section 15 (along with the device 20 therethrough) is deflected in the other direction. If the deflection arm 36 rotates too freely or not readily enough, the electrophysiologist can adjust the tension on the deflection arm 36 by rotating the tension knob 100.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A deflectable introducer for use with a device for passage into a patient's body, the introducer comprising:
   a shaft comprising a deflectable section and a distal tip section, the shaft having a central lumen through which the device can extend, the distal tip section comprising:
      a distal tip,
      a fastener configured to attach the distal tip to the deflectable section of the shaft, and
      a transition section between the fastener and the deflectable section;
   an elongated control handle defining a longitudinal axis;
   a tensile member having first and second proximal portions and a continuous distal portion, the tensile member extending from the control handle to the deflectable section and back to the control handle, wherein the control handle has a deflection assembly comprising a deflection member and a rotatable member, the deflection member being rotatable about an axis generally perpendicular to the longitudinal axis of the control handle, the rotatable member being rotationally coupled to the deflection member, the rotatable member having a first pulley engaged with the first proximal portion of the tensile member situated within the control handle and a second pulley engaged with the second proximal portion of the tensile member situated within the control handle, wherein the shaft includes first and second off-axis channels and a distal transition channel proximal of a distal end of the central lumen and extending generally transverse to the first and second off-axis channels, the distal transition channel having a semi-circular shape that extends partially around a circumference of the central lumen to connect the first and second off-axis channels, the distal portion of the tensile member extends through the first and second off-axis channels and the distal transition channel, and the distal portion of the tensile member enters each off-axis channel through a port in a sidewall of the shaft;
   wherein manipulation of the deflection member in one direction draws on the first proximal portion of the tensile member for deflecting the deflectable section of the shaft in the one direction, and manipulation of the deflection member in another direction draws on the second proximal portion of the tensile member for deflecting the deflectable section of the shaft in the other direction.

2. The deflectable introducer of claim 1, wherein the distal portion of the tensile member is a puller wire and each of the first and second proximal portions of the tensile member is a tensile fiber.

3. The deflectable introducer of claim 1, wherein the deflection assembly includes a tension knob for adjusting tension on the deflection member.

4. The deflectable introducer of claim 1, wherein the transition section of the distal tip section of the shaft is softer than the deflectable section of the shaft.

5. The deflectable introducer of claim 1, wherein the distal tip of the distal tip section of the shaft has a conical cross-section.

6. The deflectable introducer of claim 1, wherein the distal tip comprises a radiopaque material.

7. The deflectable introducer of claim 1, wherein the transition section of the distal tip section of the shaft comprises fluid ports configured to allow fluid to pass from the central lumen to outside the shaft.

8. The deflectable introducer of claim 1, wherein the fastener of the distal tip section of the shaft comprises a ring, and the distal transition channel of the shaft is located in the ring.

9. A deflectable introducer for use with a device for passage into a patient's body, the introducer comprising:
a shaft comprising a deflectable section and a distal tip section distal the deflectable section,
the distal tip section comprising:
a distal tip, and
a transition section between the distal tip and the deflectable section,
the shaft having a central lumen through which the device can extend and comprising,
a lining extending through the deflectable section and transition section, and terminating in the distal tip,
a proximal outer layer extending through the deflectable section and terminating at a proximal end of the distal tip section, and
a distal outer layer extending through the transition section, the distal outer layer being different from the proximal outer layer;
an elongated control handle defining a longitudinal axis; and
a tensile member having first and second proximal portions and a continuous distal portion, the tensile member extending from the control handle to the deflectable section and back to the control handle, and the continuous distal portion of the tensile member being wrapped around an exposed outer surface of the distal portion of the deflectable section, wherein the control handle has a deflection assembly comprising a deflection member and a rotatable member, the deflection member being rotatable about an axis generally perpendicular to the longitudinal axis of the control handle, the rotatable member being rotationally coupled to the deflection member, the rotatable member having first and second pulleys, each engaged with one of the first and second proximal tensile member portions situated within the control handle;
wherein rotation of the deflection member in one direction rotates the rotatable member such that the first pulley draws on its respective proximal tensile member portion for deflecting the deflectable section of the shaft in the one direction, and rotation of the deflection member in another direction rotates the rotatable member such that the second pulley draws on its respective proximal tensile member portion for deflecting the deflectable section of the shaft the other direction.

10. The deflectable introducer of claim 9, wherein the control handle further comprises a tension knob adapted for operator manipulation in adjusting ease at which the deflection member can be rotated.

11. The deflectable introducer of claim 9, wherein the shaft extends through the rotatable member.

12. The deflectable introducer of claim 9, wherein the distal outer layer is softer than the proximal outer layer.

13. The deflectable introducer of claim 9, wherein each of the first and second proximal portions of the tensile member comprises a connector connecting the respective first or second proximal portion to the continuous distal portion.

14. The deflectable introducer of claim 13, wherein the continuous distal portion comprises a puller wire and the first and second proximal portions each comprises a fiber.

15. The deflectable introducer claim 9, wherein the distal tip of the distal tip section of the shaft has a conical cross-section.

16. The deflectable introducer of claim 9, wherein the distal tip comprises a radiopaque material.

17. The deflectable introducer of claim 9, wherein the transition section of the distal tip section of the shaft comprises fluid ports configured to allow fluid to pass from the central lumen to outside the shaft.

18. The deflectable introducer of claim 11, wherein the rotatable member has a cutout to allow rotation of the rotatable member with the shaft extending therethrough.

19. The deflectable introducer of claim 9, wherein the shaft includes first and second off-axis channels through which the first and second proximal portions of the tensile member extend.

20. The deflectable introducer of claim 19, wherein the off-axis channels extend through the proximal outer layer and into the distal outer layer.

* * * * *

UNITED STATES PATENT AND TRADEMARK OFFICE
CERTIFICATE OF CORRECTION

| | |
|---|---|
| PATENT NO. | : 10,980,976 B2 |
| APPLICATION NO. | : 16/102008 |
| DATED | : April 20, 2021 |
| INVENTOR(S) | : Jeffrey W. Schultz |

It is certified that error appears in the above-identified patent and that said Letters Patent is hereby corrected as shown below:

In the Claims

Column 12, Line 5, Claim 9      After "shaft", Insert -- in --

Column 12, Line 21 (approx.), Claim 15      After "introducer", Insert -- of --

Signed and Sealed this
Third Day of May, 2022

Katherine Kelly Vidal
*Director of the United States Patent and Trademark Office*